United States Patent [19]

Ellman et al.

[11] Patent Number: 6,001,077
[45] Date of Patent: Dec. 14, 1999

[54] VACUUM WAND FOR SURGICAL SMOKE PLUME EVACUATION SYSTEM

[76] Inventors: Alan G. Ellman; Jon C. Garito, both of 1135 Railroad Ave., Hewlett, N.Y. 11557

[21] Appl. No.: 09/084,329

[22] Filed: May 26, 1998

[51] Int. Cl.⁶ ..................................................... A61M 1/00
[52] U.S. Cl. .............................. 604/35; 604/902; 604/19; 606/41
[58] Field of Search .................................. 604/19, 35, 45, 604/902; 606/32, 34, 42, 45, 49, 41

[56] References Cited

U.S. PATENT DOCUMENTS

| | | | |
|---|---|---|---|
| 5,160,334 | 11/1992 | Billings et al. | 606/34 |
| 5,342,349 | 8/1994 | Kaufman | 606/1 |
| 5,380,245 | 1/1995 | Reiterman et al. | 454/63 |
| 5,709,675 | 1/1998 | Williams | 606/1 |
| 5,769,702 | 6/1998 | Hanson | 454/63 |

*Primary Examiner*—Corrine McDermott
*Assistant Examiner*—Michael J. Hayes

[57] ABSTRACT

Smoke evacuation apparatus designed to provide safe and efficient filtration and evacuation of smoke plume generated by laser-surgical, electrosurgical, radiosurgical, and electrocautery devices, and a wand for use therewith. The wand comprises at its free end a tapered tip across which is mounted a mesh configured to allow air to flow freely into the wand while at the same time being capable of capturing any solid objects entrained by the suctioned air. In a preferred embodiment, the tip is tapered on both sides, and meshes mounted across both tapered sides. This has the advantage that air can be suctioned from either or both sides of the tapered tip, and also allows the wand to be used as a tongue or tissue depressor without interfering with its ability to suction smoke and plume from the surgical site.

7 Claims, 4 Drawing Sheets

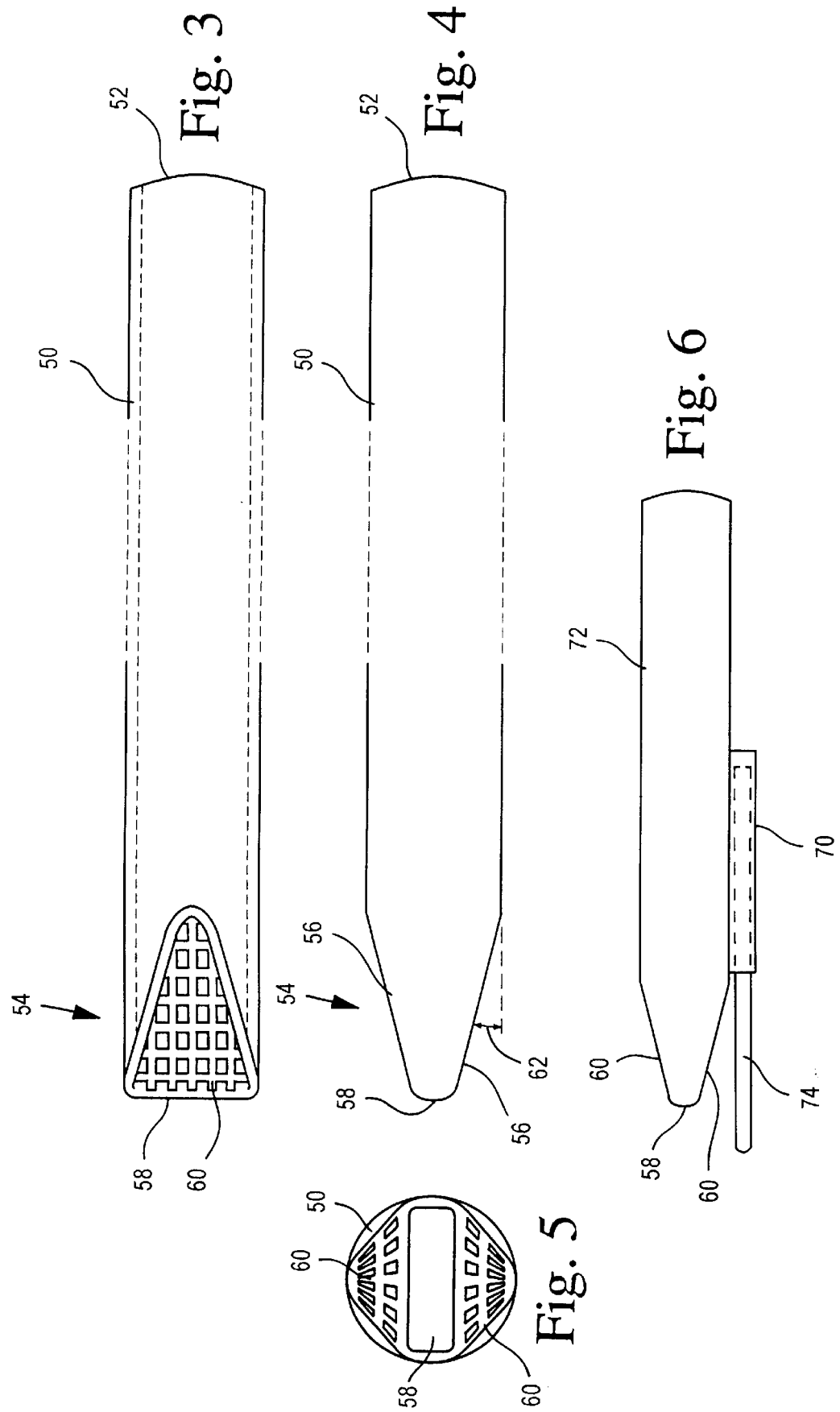

VACUUM WAND FOR SURGICAL SMOKE PLUME EVACUATION SYSTEM

RELATED APPLICATION

U.S. application, Ser. No. 09/024,435, filed Feb. 17, 1998.

BACKGROUND OF INVENTION

Surgical smoke evacuation systems are designed to capture the smoke and plume generated during surgical procedures in which there is thermal destruction of tissue or bone. The plume from vaporized tissue contains small particles and gases that could be potentially hazardous. If not evacuated the materials can become airborne and deposit in the respiratory tracts of the surgical team. The type of surgical instruments, the characteristics of tissue, and the surgeon's technique affect the quantity and characteristics of the smoke plume. A surgical smoke evacuator is in essence a vacuum pump, usually footswitch operated, that incorporates one or more filters to remove particles from the suctioned air-stream at the surgical site. A hose, typically of plastic, disposable or reusable, connects the pump to a disposable or autoclavable wand serving as a nozzle that is usually held about 5 cm. from the tissue to remove smoke generated by the surgical procedure. Because the constraints of some surgical procedures can prevent placement of the nozzle close to the tissue, smoke evacuators should capture smoke effectively at up to 15 cm. Adequate protection from potentially dangerous smoke plume can only be achieved when the plume is successfully captured before it comes into contact with the patient and surgical staff. This smoke entrainment requires that the evacuator airflow change the smoke direction and draw it into the hose via the wand. The ability of a smoke evacuator to collect the surgical plume is highly dependent on three factors; the distance of the wand from the source, the volumetric airflow entering the wand and hose, and the local velocities of the room air.

Several problems currently exist with wands that are available. As the distance of the wand from the surgical site increases, the ability of the smoke evacuator to capture the surgical plume decreases. For optimal plume evacuation efficiency, studies and manufacturers recommend that the evacuator wand be maintained within close proximity of the smoke generation site, typically within 5 cm. This close proximity prevents the plume from escaping capture, as may occur when the evacuator wand is held too far from the surgical site. Holding the evacuator wand at this close distance, however, may not always be practical or safe during the entire procedure. One of the problem that exists with current wands is that the high volumetric vacuum airflow at this close distance to delicate tissue may rip and suction tissue or suction the surgical gauze, drapes, or other surgical accessories from the surgical site and surrounding area.

An even bigger problem exists with the advent of delicate radiosurgical procedures used to excise tissue and the need to preserve these excised tissues for histological interpretation. The high volumetric vacuum may suction the tissue into the wand and through the tubing and possibly into the motor itself Not only is the excised tissue lost, but the apparatus may become contaminated by the absorbed tissue, and/or the apparatus may cause tiny pieces of the tissue to spread into the room environment, which can be dangerous to surgical personnel, especially when the tissue originates from a patient who has a communicable disease.

SUMMARY OF INVENTION

A principal object of the invention is surgical smoke evacuation apparatus that overcomes one or more of the drawbacks listed above.

This and other objects of the invention are achieved in accordance with one feature of the invention by provision of a novel wand for use with surgical smoke evacuation apparatus. The wand comprises at its free end a tapered tip across which is mounted a mesh configured to allow air to flow freely into the wand while at the same time being capable of capturing any solid objects entrained by the suctioned air.

In a preferred embodiment, the tip is tapered on both sides, and meshes mounted across both tapered sides. This has the advantage that air can be suctioned from either or both sides of the tapered tip, and also allows the wand to be used as a tongue or tissue depressor without interfering with its ability to suction smoke and plume from the surgical site.

In a further preferred embodiment, a holder is mounted on one side of the wand, the holder being configured to removably receive a conventional tongue depressor, again without interfering with its ability to suction smoke and plume from the surgical site.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

SUMMARY OF THE DRAWINGS

In the drawings:

FIG. 3 is a plan view of one form of wand in accordance with the invention for use with smoke evacuation apparatus;

FIG. 4 is a side view of the wand of FIG. 3;

FIG. 5 is an end view of the wand tip of FIG. 4;

FIG. 6 is a side view of another form of wand according to the invention;

DETAILED DESCRIPTION OF PREFERRED EMBODIMENTS

The above-identified related application, whose contents are hereby incorporated by reference, describes surgical smoke evacuation apparatus that employs two independent filters in series in the suction path. The first filter is a viral pre-filter which is capable of filtering micro-organisms bigger than 0.02 microns in size. Following the pre-filter is a charcoal filter that efficiently removes odors.

Figure 1:
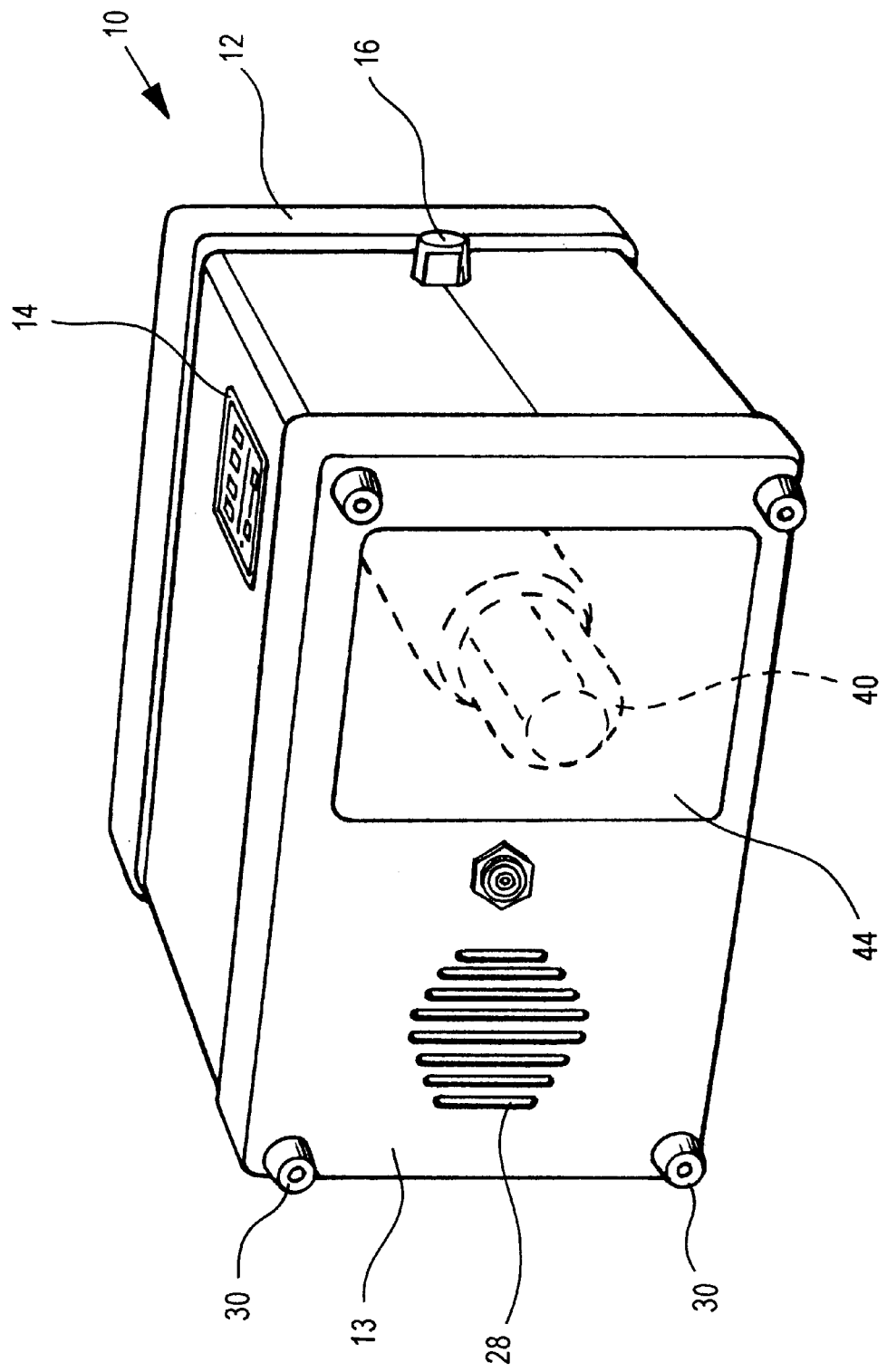
FIG. 1 is a bottom perspective view of the surgical smoke evacuation apparatus described in the related application, shown without the usual attachments.

A preferred embodiment 10 is illustrated in FIG. 1 and comprises a main housing 12, turned on its side so that its bottom 13 is visible, that provides a control panel 14 on the front side and on the right side an air inlet 16 for receiving a hose connector (see FIG. 2) mounted at the end of a plastic vacuum hose 18. Inside the housing 12 is provided a brushless DC blower motor 20 available commercially from many suppliers and having an air inlet 22 and an air outlet 24. In operation, an internal 2-stage fan (not shown) develops a suitable suction at its air inlet 22 by discharging a powerful stream of air at its outlet 24. The discharged air exits the housing via a muffler 26 and a sound-deadening mesh 27 over a vent 28 at the bottom side of the housing. Standoffs 30 provide easy flow of the exhaust stream to the ambient. The speed of the motor 20 may be controlled in a known manner. Typically, the suction generated is inversely proportional to the air flow rate.

The vacuum hose 18 is connected at one end to the housing air inlet 16, and at the opposite end to an external pre-filter 32. Preferably, the pre-filter 32 comprises a viral paper filter capable of filtering micro-organisms exceeding 0.02 microns, and is also available commercially from many suppliers. The viral paper filter is mounted inside a small housing 34 which is not meant to be opened and the housing and assembled filter 32 is easily removed and replaced by any user of the apparatus. To the air inlet side of the pre-filter 32 is connected a wand 36 via its air outlet and with the wand 36 having at its air inlet a mesh tip 38 which is positioned by the practitioner at the site where the smoke plume is generated.

Figure 2:
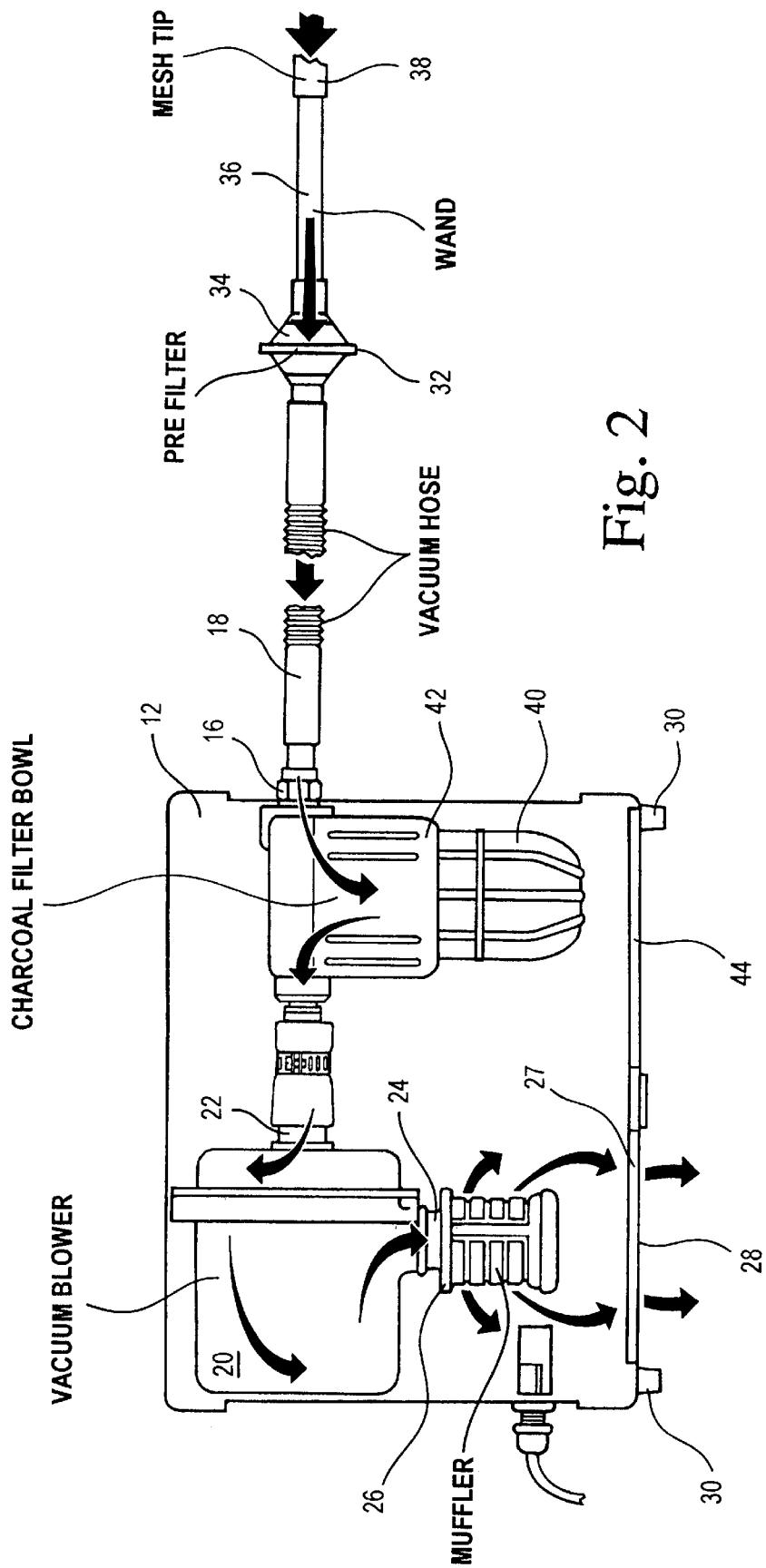
FIG. 2 is an interior view of the smoke evacuation apparatus of FIG. 1 with attachments illustrating the air flow through the apparatus.

Inside the main housing 12, in series in the air flow shown by the large arrows, is a conventional charcoal filter 40 mounted in a filter canister or bowl 42. As shown in FIG. 2, the air flow from the vacuum hose 18 after entering the main housing is directed to one side of the filter bowl 42, passes through the charcoal filter 40 in the process and is then directed to the motor air inlet 22. The filter bowl is located near the base of the main housing 12 behind a removable panel 44 which allows access to the charcoal filter canister 40 for replacement when necessary. In FIG. 1, the removable panel is 44 shown as if it were transparent so that the charcoal canister 40 behind it is visible.

The present invention is directed to the wand element of the surgical smoke evacuator.

A preferred embodiment of the invention is illustrated in FIGS. 3–5, and comprises a hollow tube 50 whose first end 52, its air outlet, is configured to attach to the hose 18 or prefilter 34. At its second end 54, its air inlet, also referred to herein as the wand tip, the tube tapers 56 on opposite sides to a bottom closed offend 58. The tapered sides 56 are generally flat and are each covered with a mesh 60. The taper angle indicated by reference numeral 62 is preferably about 15° but can vary between about 10° and 30°.

The wand 50 is generally made of a hard, stiff plastic in a variety of diameters to match the hose diameter. The hoses 18 are typically available in six and ten inch lengths; with diameters of ¼, ⅜, ⅞, and 1 ¼ inches. The length of the mesh along the flat side 56 is, for example, about 1–2 inches.

The mesh 60 at the wand tip can likewise be made of plastic. The preferred dimensions of the mesh openings are about 0.085±0.005 in width by 0.120±0.005 in length, but can be varied from about 0.05 to about 0.2 inches. (All dimensions are given in inches.) This mesh design built into the wand tip allows air to flow through freely and prevents tissue, debris, and gauze from being vacuumed into the wand, tubing or motor. The angled mesh design built into the wand tip allows the surgeon and staff members to easily view the surgical site and workspace of the surgeon while the wand is present in the vicinity of the surgical site to remove any generated smoke or plume. Another advantage of the angled sides of the wand tip is that the tip can also be utilized as a tissue depressor or retractor, replacing a tongue depressor or tissue retractor.

Figure 7:
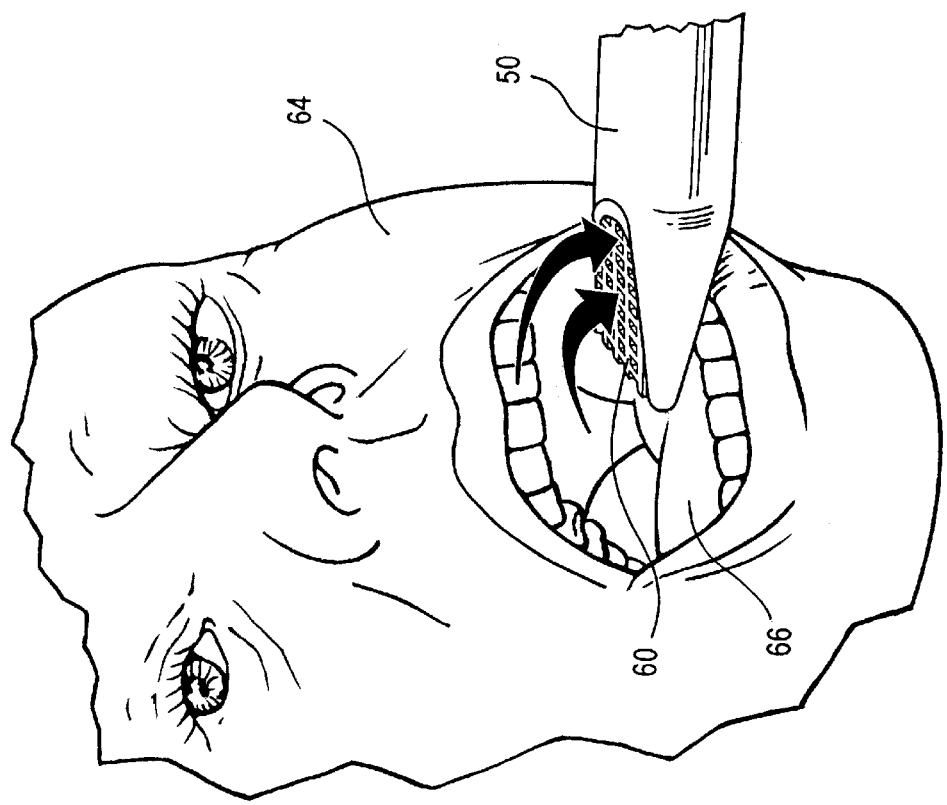

This is illustrated in FIG. 7 which shows the wand 50 of the invention inserted in the mouth of a patient 64 and serving simultaneously as a tongue depressor. While performing that function, with one angled side 56 in contact with the patient's tongue 66, the mesh side 60 on top is free and thus capable of carrying out its suction function. Even though one side of the angled mesh side of the wand is pressed onto the tongue and thus may be incapable of generating any significant suction, air can still be drawn from the other side on top and free of obstructions. This is an important advantage as it eliminates the need for an additional staff member to hold a tongue depressor or tissue retractor.

Figure 8:
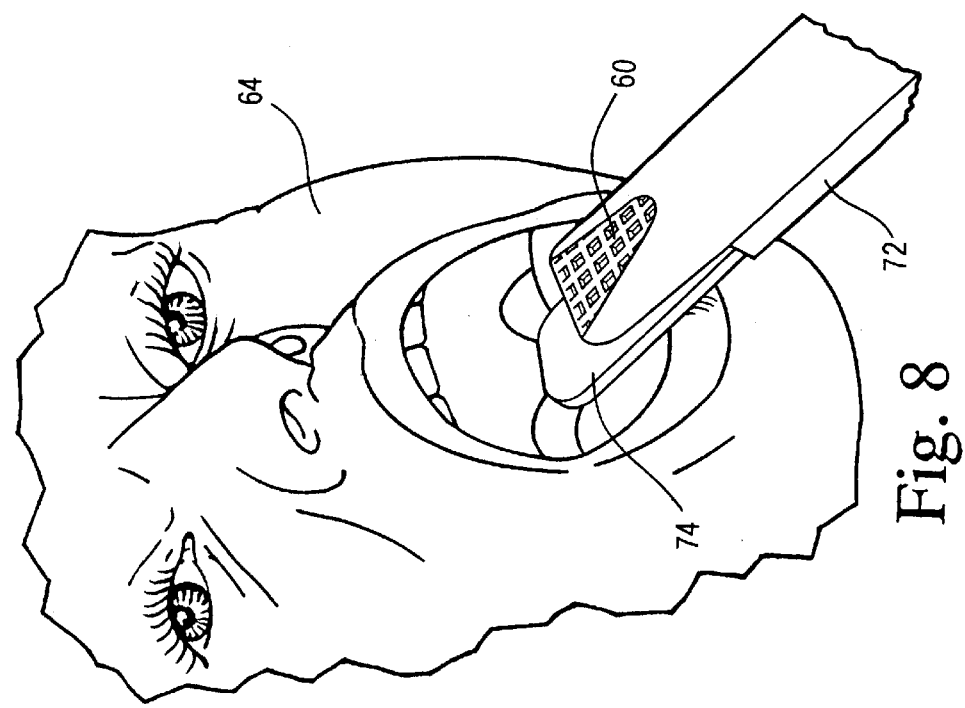
FIGS. 7 and 8 are perspective views illustrating use of the wands of FIGS. 3 and 6, respectively.

FIG. 6 shows a variant. In this case, a holder 70 is attached to a wand 72 having at its tip oppositely tapered sides each covered with a mesh 60. The holder 70 is capable of removably supporting a tongue depressor 74. FIG. 8 illustrates its use. In this case, the tongue depressor 74 is used to hold the tongue or other tissue down while the surgeon works on the patient 64. As a result, both sides of the meshed wand tip are available for suctioning out undesired smoke or plume. After use, the tongue depressor 74 may be removed and disposed of and replaced by a fresh sterile tongue depressor 74 for the next patient.

An effective surgical smoke evacuator uses a high flow and intake velocity to capture the smoke with the wand, draw it through the hose, pass it through the filter and recirculate it back into the operating room. The provision of the wand element of the invention allows effective suction to be generated at its inlet tip via one or both of the mesh sides without fear of interrupting the suction function or undesirably ingesting tissue or other surgical paraphernalia.

The apparatus of the invention efficiently removes smoke from a surgical operatory area for better visibility, protects a medical team from smoke plume containing viruses, eliminates for the most part unpleasant smoke and odors, and also draws cool air over the surgical site.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A wand for use with smoke or plume evacuation apparatus having a hose, comprising:
   a) a hollow tube having an air outlet end for connection to the hose and an air inlet end,
   b) said wand air inlet end having oppositely-directed, generally flat tapered sides extending from a common front end,
   c) air-permeable meshes having openings and mounted on and closing off each of the tapered sides such that air entering the wand at its air inlet must pass through the mesh openings.

2. A wand for use with smoke or plume evacuation apparatus as claimed in claim 1, wherein the tapered sides of said wand air inlet are at an angle of between about 10–30°.

3. A wand for use with smoke or plume evacuation apparatus as claimed in claim 1, wherein the air-permeable mesh has openings varying between about 0.05 to about 0.2 inches.

4. A wand for use with smoke or plume evacuation apparatus as claimed in claim 1, wherein the wand at its air outlet end has an outer diameter selected from the group consisting of ¼, ⅜, ⅞, and 1¼ inches.

5. A wand for use with smoke or plume evacuation apparatus as claimed in claim 1, wherein the mesh has mesh openings about 0.085±0.005 in width by 0.120±0.005 in length, all in inches.

6. Apparatus for smoke plume evacuation arising from operation of laser-surgical, electrosurgical, radiosurgical, and electrocautery devices, comprising:

a) a housing having an air inlet and an air outlet, b) a removable odor-removing filter canister having an air inlet and an air outlet inside the housing, c) means connecting the canister air inlet to the housing air inlet, d) motor means in the housing for forcing air to flow between a motor air inlet and a motor air outlet establishing a suction at the motor air inlet, e) the motor means being positioned such that air from its air outlet can flow to and out of the housing air outlet, f) means connecting the motor air inlet to the canister air outlet, g) a vacuum hose connected to the housing air inlet whereby suction is available at the hose when the apparatus is activated, h) a viral filter assembly external to the housing and removably connected to the vacuum hose and in series with air flow through the hose, i) a wand connected to the viral filter assembly, said wand comprising:

i) a hollow tube having an air outlet end for connection to the viral filter assembly and an air inlet end, ii) said wand air inlet end having oppositely-directed flat tapered sides extending outwardly from a common front end, iii) meshes with air-permeable openings mounted on and closing off both of the tapered sides such that air entering the wand at its air inlet must pass through the mesh, iv) said wand air inlet end being configured such that, when either flat side is placed in contact with a patient's tissue, at least some of the air-permeable mesh openings on the opposite flat side will remain unobstructed.

7. Apparatus as claimed in claim 6, wherein the tapered sides of said wand air inlet are at an angle of between about 10–30°, and the air-permeable mesh has openings varying between about 0.05 to about 0.2 inches.

\* \* \* \* \*